United States Patent
Smoliga et al.

(10) Patent No.: US 7,091,340 B2
(45) Date of Patent: Aug. 15, 2006

(54) POLYMORPHS

(75) Inventors: John A. Smoliga, Brookfield, CT (US); Jana Vitous, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 11/010,975

(22) Filed: Dec. 13, 2004

(65) Prior Publication Data

US 2005/0137195 A1 Jun. 23, 2005

Related U.S. Application Data

(60) Provisional application No. 60/530,834, filed on Dec. 18, 2003.

(51) Int. Cl.
    *C07D 413/02* (2006.01)
(52) U.S. Cl. ..................................................... 544/140
(58) Field of Classification Search ................ 544/140; 514/235.5
    See application file for complete search history.

(56) References Cited

U.S. PATENT DOCUMENTS

| 6,319,921 B1 | 11/2001 | Cirillo |
| 6,525,046 B1 * | 2/2003 | Cirillo et al. ............ 514/227.8 |
| 6,583,282 B1 * | 6/2003 | Zhang et al. ................ 544/124 |
| 6,916,924 B1 | 7/2005 | Tan et al. |
| 2003/0232865 A1 * | 12/2003 | Cirillo et al. ................ 514/370 |

OTHER PUBLICATIONS

US Pharmacopia #23, National Formulary #18 (1995).*
Brittain in Polymorphism in Pharmaceutical Solids, Marcel Dekker Inc.,p. 236 (1999).*
Cheronis, Semimicro Experimental Organic Chemistry, Ch. 5: Purification of Solids by Crystallization, p. 31-45 (1958).*

* cited by examiner

*Primary Examiner*—Kamal A. Saeed
*Assistant Examiner*—Andrew B. Freistein
(74) *Attorney, Agent, or Firm*—Michael P. Morris; Anthony P. Bottino; Philip I. Datlow

(57) ABSTRACT

Disclosed are polymorphs of 1-(5-tert-butyl-2-p-tolyl-2H-pyrazol-3-yl)-3-[4-(2-morpholin-4-yl-ethoxy)-naphthalen-1-yl]-urea and processes from making the same.

3 Claims, 2 Drawing Sheets

POLYMORPHS

RELATED APPLICATION DATA

This application claims benefit to U.S. provisional application No. 60/530,834 filed Dec. 18, 2003.

BACKGROUND OF THE INVENTION

1. Technical Field

This invention relates to a polymorph of a p38 MAP kinase inhibitor useful for treating cytokine mediated diseases.

2. Background Information p38 MAPK is an integral enzyme necessary for the generation of many pro-inflammatory cytokines, eg., TNF-α in vitro and in vivo. Inhibitors of this enzyme would therefore be useful in treating cytokine mediated diseases. A potent inhibitor of this enzyme, BIRB 796 BS, is described in U.S. Pat. No. 6,319,921, example no. 8.

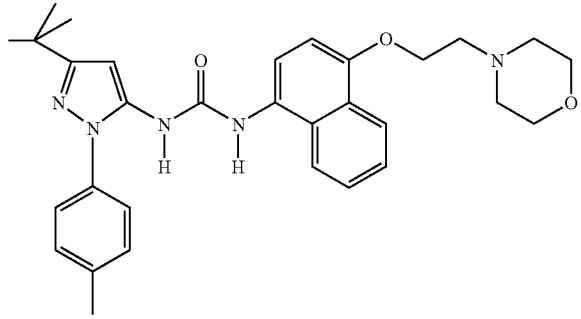

1-(5-tert-butyl-2-p-tolyl-2H-pyrazol-3-yl)-3-[4-(2-morpholin-4-yl-ethoxy)-naphthalen-1-yl]-urea (hereinafter, "BIRB 796").

U.S. Pat. No. 6,583,282 and related U.S. patent application Ser. No. 10/300,448 disclose conditions which produce a single polymorph known as Form IV. The same polymorph Form IV is disclosed in U.S. Pat. No. 6,565,880 directed to formulations of BIRB 796. One of the desirable characteristics of a preferred polymorph form is that it be more thermodynamically stable.

BRIEF SUMMARY OF THE INVENTION

The work cited above supports the principle that a more thermodynamically stable polymorph form of BIRB 796 BS would be more desirable as a drug product.

It is therefore an object of the invention to provide polymorph form of BIRB 796 BS designated Form VI as described in detail herein below.

It is a further object of the invention to provide processes of making said polymorph.

DETAILED DESCRIPTION OF THE INVENTION

Figure 1:
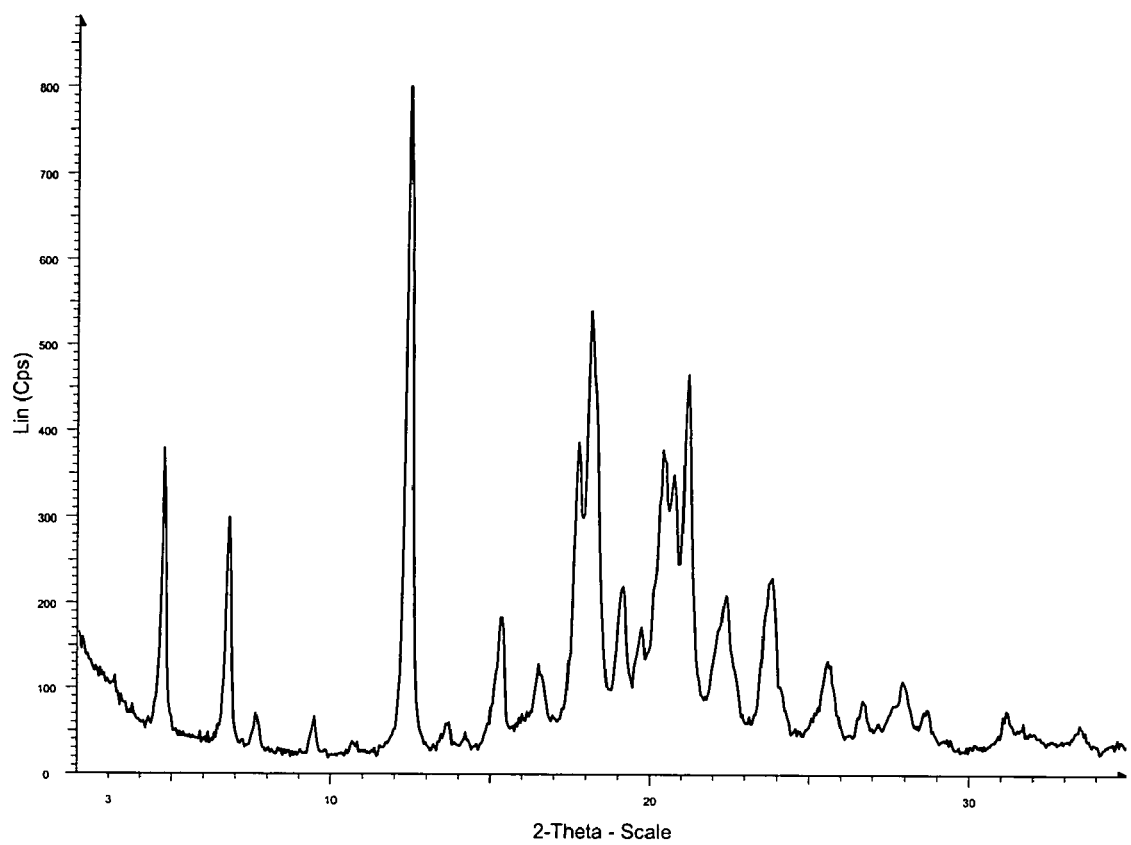
FIG. 1 shows a typical x-ray powder diffraction pattern obtained from BIRB 796 BS Form VI.
Figure 2:
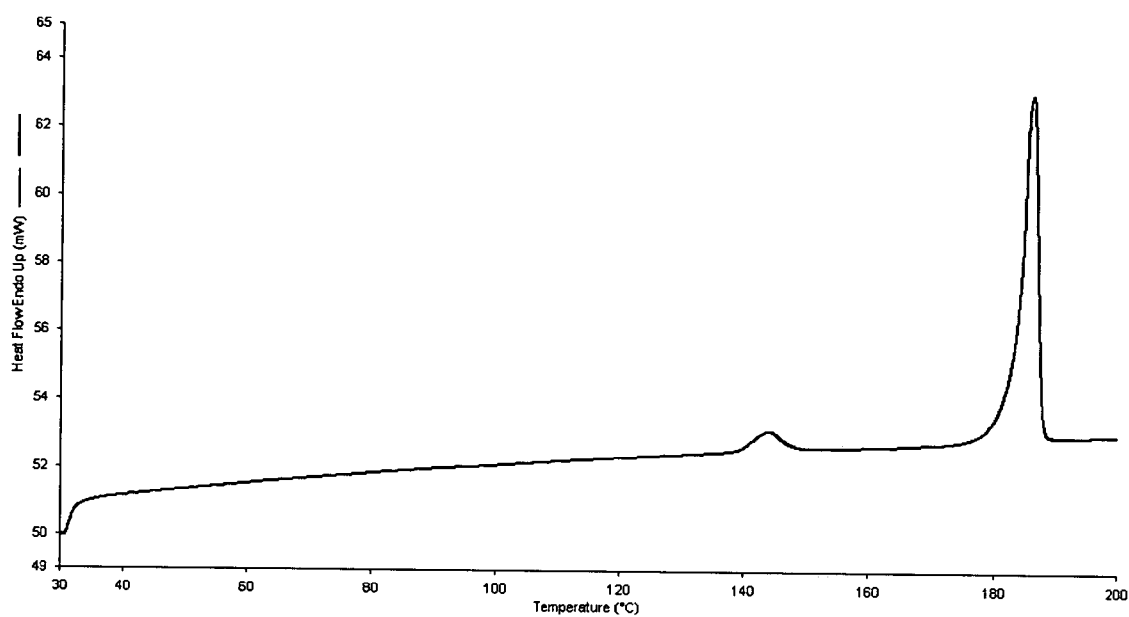
FIG. 2 shows a typical differential scanning calorimetry thermal curve obtained from BIRB 796 BS Form VI at a heating rate of 10° C./min.

In one aspect of the invention, there is provided a polymorph Form VI of BIRB 796 possessing a solid-solid polymorphic transformation in the range of 138–145° C. to Form VII which subsequently melts in the range of 177–186° C.

In a more preferred embodiment, the aforementioned form VI polymorph possesses the DSC above and the following XRPD data in Table I:

TABLE I

| Angle 2-Theta ° | Intensity % % |
|---|---|
| 4.7 | 48 |
| 6.8 | 38 |
| 12.5 | 100 |
| 15.3 | 23 |
| 17.8 | 49 |
| 18.2 | 68 |
| 19.1 | 28 |
| 21.2 | 58 |
| 22.4 | 27 |
| 23.8 | 29 |

BIRB 796 Form VI XRPD Data using Cu CuKα radiation 1.54 Å).

It shall be understood that a polymorph with a m.p. of 177–186° C. can have deviations of diffraction data and DSC range data mentioned above and are within the scope of the present invention.

In another aspect of the invention there is provided a process of preparing a BIRB 796 polymorph form VI as described hereinabove, said process comprising:

Dissolving BIRB 796 in a solvent chosen from ethyl acetate, butyl acetate, isobutyl acetate, isopropyl acetate, propyl acetate and t-butyl acetate at reflux temperature;

preferably the solvent is ethyl acetate;

cooling the solution to about room temperature and subsequently collecting the crystallizing solid, preferably by filtration.

EXAMPLES

Crystalline samples recovered from ethyl acetate, butyl acetate, isobutyl acetate, isopropyl acetate, propyl acetate and t-butyl acetate exhibit two endotherms by DSC in the ranges of 138–145° C. and 177–186° C.

Thermomicroscopical experiments conducted on the propyl acetate sample show that the endotherm observed in the 138–139° C. region is a solid-solid polymorphic transformation and that the endotherm observed in the 183–184° C. is a melt. This establishes that the samples crystallized from acetate solvents are a unique polymorph (Form VI) which undergoes a solid-solid transformation to a higher temperature polymorph (Form VII) at about 138–139° C. Form VII then melts at 183–184° C. If allowed to cool prior to melting the solid-solid transformation is reversible whereby Form VII reverts to Form VI below 138° C.

DSC experiments conducted on the isopropyl acetate sample show two endothermic events with extrapolated onsets in the range of about 139° C. and 185° C. confirming the events discussed above. Thermogravimetric analysis (TGA) conducted on this sample shows no detectable weight loss in the range of 29° C.–250° C., indicating that this is not a solvated species. NMR data obtained on the isopropyl acetate sample indicate that this material is consistent with the structure of BIRB 796. Temperature stage XRPD studies conducted on the propyl acetate sample confirms the thermomicroscopy studies above.

Thermodynamic Stability of Form VI:

Microscopical solution phase transformation experiments conducted on Forms IV and VI establishes that Form VI is more thermodynamically stable at room temperature relative to Form IV. Solubility vs. temperature profile experiments conducted on Forms IV and VI establishes that these two forms are monotropically related within the temperature range of the experiment (one form is more stable than the other at all temperatures studied) and confirms that Form VI is more thermodynamically stable relative to Form IV.

Methods of Use

The above mentioned physical characteristics of Form VI show that it is desirable as a drug product, particularly useful for treating cytokine mediated diseases, including the following conditions and diseases: osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The polymorph of the invention may also be useful for anticoagulant or fibrinolytic therapy (and the diseases or conditions related to such therapy) as described in the provisional application No. 60/403,422.

The polymorph of the invention is a p38 MAP kinase inhibitors and therefore be useful for treating diseases associated with p38 MAP kinase such as inflammatory and oncological diseases. Oncological diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the polymorph compound may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The polymorph compound may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. Pat. No. 6,565,880 and U.S. application Ser. No. 10/214,782, each incorporated by reference herein in their entirety. Advantageously, the polymorph compound may then be administered together in a single dosage form. In some embodiments, the pharmaceutical compositions comprising such combinations of compounds contain at least about 5%, but more preferably at least about 20%, of a polymorph (w/w) or a combination thereof. The optimum percentage (w/w) of a polymorph compound of the invention may vary and is within the purview of those skilled in the art. Alternatively, the polymorph compound may be administered separately (either serially or in parallel). Separate dosing allows for greater flexibility in the dosing regime.

As mentioned above, dosage forms of the polymorph compound described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

All literature references and patent publications/applications cited in this application are hereby incorporated by reference in their entirety.

What is claimed is:

1. A polymorph form VI of the compound

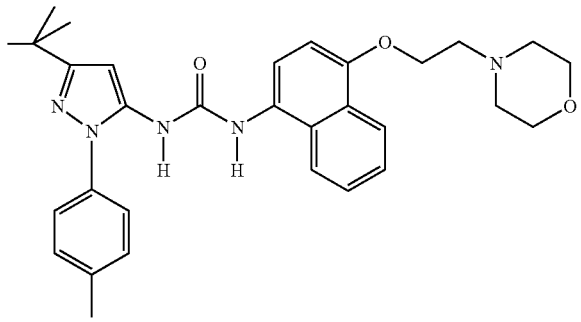

which possesses the following XRPD data in Table I:

TABLE I

| Angle 2-Theta ° | Intensity % |
|---|---|
| 4.7 | 48 |
| 6.8 | 38 |
| 12.5 | 100 |
| 15.3 | 23 |
| 17.8 | 49 |
| 18.2 | 68 |
| 19.1 | 28 |
| 21.2 | 58 |
| 22.4 | 27 |
| 23.8 | 29 | wherein the XRPD Data is using Cu CuKα radiation (1.54 Å) and wherein said polymorph has a solid-solid polymorphic transformation at a temperature of 138–145° C. which subsequently melts at a temperature of 177–186° C.

2. A process of preparing a polymorph form VI of the compound

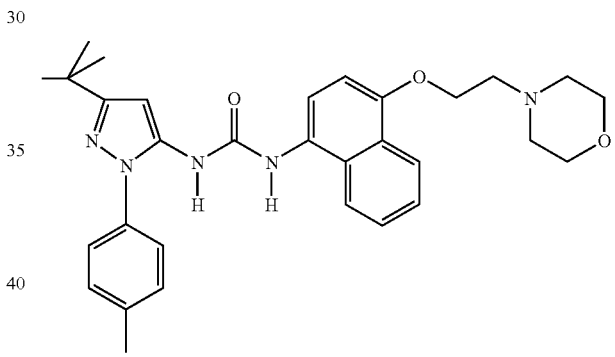

according to claim 1, said process comprising:
dissolving the compound in a solvent chosen from ethyl acetate, butyl acetate, isobutyl acetate, isopropyl acetate, propyl acetate and t-butyl acetate at reflux temperature;
cooling the solution to about room temperature and subsequently collecting the crystallizing solid.

3. The process according to claim 2, wherein the solvent is ethyl acetate.

* * * * *